US007833384B2

(12) United States Patent
Weerawarna

(10) Patent No.: US 7,833,384 B2
(45) Date of Patent: Nov. 16, 2010

(54) METHOD FOR MAKING FIBER HAVING BIODEGRADABLE SUPERABSORBENT PARTICLES ATTACHED THERETO

(75) Inventor: S Ananda Weerawarna, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 369 days.

(21) Appl. No.: 12/165,055

(22) Filed: Jun. 30, 2008

(65) Prior Publication Data

US 2009/0321030 A1 Dec. 31, 2009

(51) Int. Cl.
*D21H 17/24* (2006.01)
*C08B 15/10* (2006.01)
*C08B 30/00* (2006.01)

(52) U.S. Cl. ..................... 162/175; 162/177; 264/109; 264/140; 536/97; 536/98; 536/106

(58) Field of Classification Search ................. 162/175, 162/177; 264/109, 115, 141, 142, 144, 145, 264/163, 180, 183, 187, 211.18, 211.11, 264/211.16, 211.19; 536/97, 98, 106; 604/374, 604/375, 376, 910; 428/359, 402
See application file for complete search history.

(56) References Cited

U.S. PATENT DOCUMENTS

| 3,645,836 | A | | 2/1972 | Torr |
| 4,028,290 | A | | 6/1977 | Reid |
| 4,128,692 | A | | 12/1978 | Reid |
| 4,143,163 | A | | 3/1979 | Hutchinson et al. |
| 4,273,118 | A | | 6/1981 | Smith |
| 4,319,956 | A | | 3/1982 | Snyder et al. |
| 4,497,930 | A | | 2/1985 | Yamasaki et al. |
| 4,605,401 | A | | 8/1986 | Chemilir et al. |
| 4,624,868 | A | | 11/1986 | Muller |
| 4,693,713 | A | | 9/1987 | Chmelir |
| 4,952,550 | A | | 8/1990 | Wallach et al. |
| 4,959,341 | A | | 9/1990 | Wallach |
| 4,966,694 | A | | 10/1990 | Namikoshi et al. |
| 5,231,122 | A | | 7/1993 | Palumbo et al. |
| 5,384,179 | A | * | 1/1995 | Roe et al. ............. 428/192 |
| 5,425,725 | A | | 6/1995 | Tanzer et al. |
| 5,470,964 | A | | 11/1995 | Qin |
| 5,498,705 | A | | 3/1996 | Qin |
| 5,550,189 | A | | 8/1996 | Qin et al. |
| 5,589,256 | A | * | 12/1996 | Hansen et al. ............. 442/417 |
| 5,612,411 | A | | 3/1997 | Gross |
| 5,672,418 | A | * | 9/1997 | Hansen et al. ............. 442/70 |
| 5,688,776 | A | | 11/1997 | Bauer et al. |
| 5,736,595 | A | | 4/1998 | Gunther et al. |
| 5,801,116 | A | | 9/1998 | Cottrell et al. |
| 5,847,031 | A | | 12/1998 | Klimmek et al. |
| 6,051,317 | A | | 4/2000 | Brueggemann et al. |
| 6,162,541 | A | | 12/2000 | Chou et al. |
| 6,296,936 | B1 | | 10/2001 | Yahiaoui et al. |
| 6,331,619 | B1 | | 12/2001 | Besemer et al. |
| 6,339,039 | B1 | | 1/2002 | Porath et al. |
| 6,387,978 | B2 | | 5/2002 | Ronan et al. |
| 6,436,508 | B1 | | 8/2002 | Ciammaichella et al. |
| 6,524,348 | B1 | | 2/2003 | Jewell et al. |
| 6,562,743 | B1 | | 5/2003 | Cook et al. |
| 6,689,934 | B2 | | 2/2004 | Dodge, II et al. |
| 6,713,460 | B2 | | 3/2004 | Huppe |
| 6,730,722 | B1 | | 5/2004 | Eck et al. |
| 6,765,042 | B1 | | 7/2004 | Thornton et al. |
| 6,846,924 | B1 | | 1/2005 | Malmgren et al. |
| 6,998,367 | B2 | * | 2/2006 | Qin ........................... 502/400 |
| 7,153,904 | B2 | | 12/2006 | Richardson et al. |
| 7,306,039 | B2 | | 12/2007 | Wang et al. |
| 7,321,007 | B2 | | 1/2008 | Gagliardi et al. |
| 7,407,912 | B2 | | 8/2008 | Mertens et al. |
| 7,615,579 | B2 | | 11/2009 | Joy et al. |
| 2003/0027787 | A1 | | 2/2003 | Couture |
| 2003/0068944 | A1 | | 4/2003 | Carlucci et al. |
| 2003/0144642 | A1 | | 7/2003 | Dopps et al. |
| 2003/0232965 | A1 | | 12/2003 | Bergeron |
| 2004/0024092 | A1 | | 2/2004 | Sorens et al. |
| 2004/0157734 | A1 | | 8/2004 | Mertens et al. |
| 2004/0236260 | A1 | | 11/2004 | Griffiths et al. |
| 2005/0153123 | A1 | | 7/2005 | Herfert et al. |
| 2005/0155491 | A1 | | 7/2005 | Faust et al. |
| 2005/0214541 | A1 | | 9/2005 | Berrada et al. |

(Continued)

FOREIGN PATENT DOCUMENTS

WO  WO 2000/21581  4/2000

(Continued)

*Primary Examiner*—Eric Hug
*Assistant Examiner*—Peter Chin
(74) *Attorney, Agent, or Firm*—John M. Crawford

(57) ABSTRACT

A method for making fibers having particles attached thereto, comprising blending a carboxyalkyl cellulose and a starch in water to provide an aqueous gel; treating the aqueous gel with a first crosslinking agent to provide a crosslinked gel; drying the crosslinked gel to provide a solid; comminuting the solid to provide a plurality of particles; combining at least a portion of the plurality of particles with a aqueous dispersion comprising cellulose fibers and a first water-miscible solvent and, optionally, a second crosslinking agent, to provide a mixture comprising swollen particles and cellulose fibers; and adding a second water-miscible solvent to the mixture to provide fibers having particles attached thereto.

18 Claims, 3 Drawing Sheets

U.S. PATENT DOCUMENTS

| | | |
|---|---|---|
| 2006/0142477 A1 | 6/2006 | Glasser |
| 2006/0147689 A1 | 7/2006 | Wallajapet et al. |
| 2006/0165762 A1 | 7/2006 | Plaut et al. |
| 2007/0093907 A1 | 4/2007 | Goupil et al. |
| 2007/0179291 A1 | 8/2007 | Thibodeau et al. |
| 2008/0009616 A1 | 1/2008 | Frank et al. |
| 2008/0078514 A1 | 4/2008 | Weerawarna et al. |
| 2008/0078515 A1 | 4/2008 | Weerawarna et al. |
| 2008/0079187 A1 | 4/2008 | Weerawarna et al. |
| 2008/0079188 A1 | 4/2008 | Weerawarna et al. |
| 2008/0081165 A1 | 4/2008 | Weerawarna et al. |
| 2008/0081189 A1 | 4/2008 | Weerawarna et al. |
| 2008/0081190 A1 | 4/2008 | Weerawarna et al. |
| 2008/0081191 A1 | 4/2008 | Weerawarna et al. |
| 2008/0081843 A1 | 4/2008 | Weerawarna et al. |
| 2008/0082064 A1 | 4/2008 | Luo et al. |
| 2008/0082065 A1 | 4/2008 | Weerawarna et al. |
| 2008/0082066 A1 | 4/2008 | Luo et al. |
| 2008/0082067 A1 | 4/2008 | Weerawarna et al. |
| 2008/0082069 A1 | 4/2008 | Qin et al. |
| 2008/0314537 A1 | 12/2008 | Weerawarna et al. |
| 2009/0099541 A1* | 4/2009 | Qin et al. .............. 604/376 |
| 2009/0321029 A1 | 12/2009 | Weerawarna |
| 2009/0321030 A1 | 12/2009 | Weerawarna |
| 2009/0325799 A1 | 12/2009 | Weerawarna |
| 2009/0325800 A1 | 12/2009 | Weerawarna |

FOREIGN PATENT DOCUMENTS

| | | |
|---|---|---|
| WO | WO 2005/123781 | 12/2005 |
| WO | 2006/079221 A1 | 8/2006 |
| WO | WO 2006/079221 | 8/2006 |
| WO | 2006/119638 A1 | 11/2006 |
| WO | WO 2006/119638 | 11/2006 |

* cited by examiner

METHOD FOR MAKING FIBER HAVING BIODEGRADABLE SUPERABSORBENT PARTICLES ATTACHED THERETO

BACKGROUND OF THE INVENTION

Personal care absorbent products, such as infant diapers, adult incontinent pads, and feminine care products, typically contain an absorbent core that includes superabsorbent polymer particles distributed within a fibrous matrix. Superabsorbents are water-swellable, generally water-insoluble absorbent materials having a high absorbent capacity for body fluids. Superabsorbent polymers (SAPs) in common use are mostly derived from acrylic acid, which is itself derived from petroleum oil, a non-renewable raw material. Acrylic acid polymers and SAPs are generally recognized as not being biodegradable. Despite their wide use, some segments of the absorbent products market are concerned about the use of non-renewable petroleum oil-derived materials and their non-biodegradable nature. Acrylic acid based polymers also comprise a meaningful portion of the cost structure of diapers and incontinent pads. Users of SAP are interested in lower cost SAPs. The high cost derives in part from the cost structure for the manufacture of acrylic acid which, in turn, depends upon the fluctuating price of petroleum oil. Also, when diapers are discarded after use they normally contain considerably less than their maximum or theoretical content of body fluids. In other words, in terms of their fluid holding capacity, they are "over-designed". This "over-design" constitutes an inefficiency in the use of SAP. The inefficiency results in part from the fact that SAPs are designed to have high gel strength (as demonstrated by high absorbency under load or AUL). The high gel strength (upon swelling) of currently used SAP particles helps them to retain a lot of void space between particles, which is helpful for rapid fluid uptake. However, this high "void volume" simultaneously results in there being a lot of interstitial (between particles) liquid in the product in the saturated state. When there is a lot of interstitial liquid the "rewet" value or "wet feeling" of an absorbent product is compromised.

In personal care absorbent products, U.S. southern pine fluff pulp is commonly used in combination with the SAP. This fluff is recognized worldwide as the preferred fiber for absorbent products. The preference is based on the fluff pulp's advantageous high fiber length (about 2.8 mm) and its relative ease of processing from a wetland pulp sheet to an airlaid web. Fluff pulp is also made from renewable and biodegradable cellulose pulp fibers. Compared to SAP, these fibers are inexpensive on a per mass basis, but tend to be more expensive on a per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak acquired liquid because liquid is not effectively retained in such a fibrous absorbent core.

Superabsorbent produced in fiber form has a distinct advantage over particle forms in some applications. Such superabsorbent fiber can be made into a pad form without added non-superabsorbent fiber. Such pads will also be less bulky due to elimination or reduction of the non superabsorbent fiber used. Liquid acquisition will be more uniform compared to a fiber pad with shifting superabsorbent particles.

A need therefore exists for a fibrous superabsorbent material that is simultaneously made from a biodegradable renewable resource like cellulose that is inexpensive. In this way, the superabsorbent material can be used in absorbent product designs that are efficient. These and other objectives are accomplished by the invention set forth below.

SUMMARY OF THE INVENTION

The invention provides a method for making fibers having particles attached thereto, comprising blending a carboxyalkyl cellulose and a starch in water to provide an aqueous gel; treating the aqueous gel with a first crosslinking agent to provide a crosslinked gel; drying the crosslinked gel to provide a solid; comminuting the solid to provide a plurality of particles; combining at least a portion of the plurality of particles with a aqueous dispersion comprising cellulose fibers and a first water-miscible solvent and, optionally, a second crosslinking agent, to provide a mixture comprising swollen particles and cellulose fibers; and adding a second water-miscible solvent to the mixture to provide fibers having particles attached thereto. In one embodiment, the second crosslinking agent is added after adding the second water-miscible solvent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
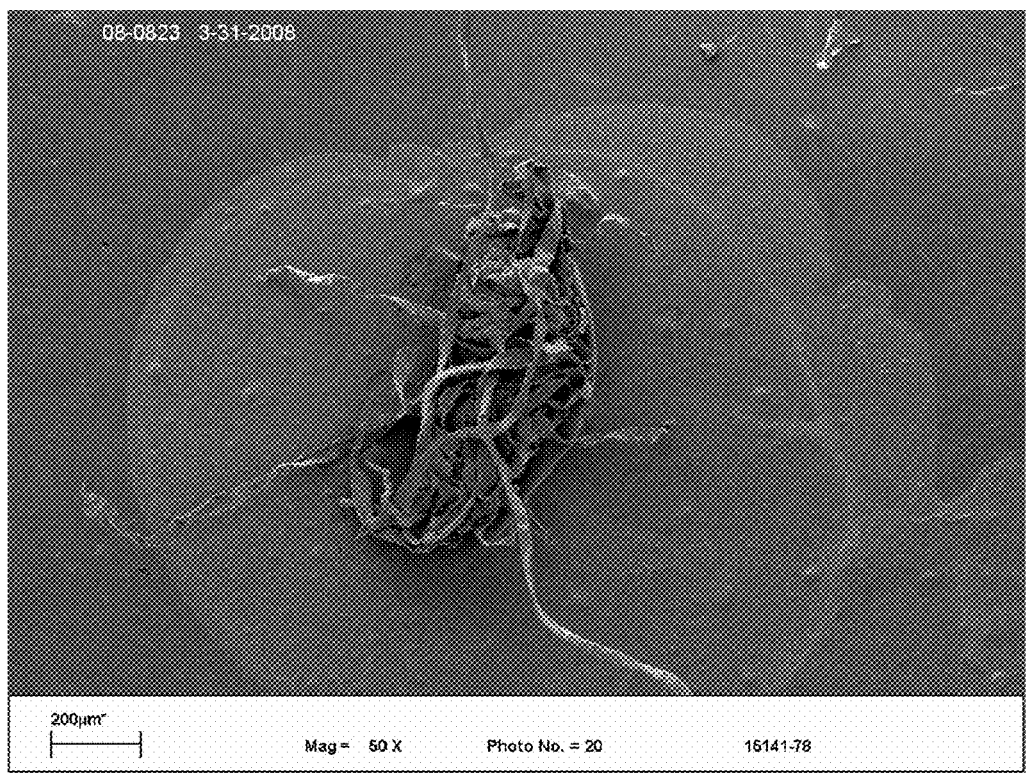
FIG. 1 is a scanning electron microscope photograph (50×) of representative fibers having particles attached thereto (Sample 4, Table 2) formed in accordance with the present invention.

In one aspect, the present invention provides a method for making a composition of cellulose fibers having superabsorbent particles attached thereto. The method includes the steps of (a) blending a carboxyalkyl cellulose and a starch in water to provide an aqueous gel; (b) treating the aqueous gel with a first crosslinking agent to provide a crosslinked gel; (c) drying the crosslinked gel to provide a solid; (d) comminuting the solid to provide a plurality of particles; (e) combining at least a portion of the plurality of particles with a aqueous dispersion comprising cellulose and a first water-miscible solvent and, optionally, a second crosslinking agent, to provide a mixture comprising swollen particles and cellulose fibers; and (f) adding a second water-miscible solvent to the mixture to provide fibers having particles attached thereto.

The fibers having particles attached thereto can be obtained by filtration. The method can further include drying the fibers having particles attached thereto to provide partially-dried fibers having particles attached thereto (30-50% consistency). The partially-dried fibers having particles attached thereto can be fiberized to provide partially-dried fiberized fibers having particles attached thereto. The partially-dried fiberized fibers having particles attached thereto can be further dried to provide dried, fiberized fibers having particles attached thereto.

In the process, a carboxyalkyl cellulose and a starch are blended in water to provide an aqueous get. Suitable carboxyalkyl celluloses have a degree of carboxyl group substitution of from about 0.3 to about 2.5, and in one embodiment have a degree of carboxyl group substitution of from about 0.5 to about 1.5. In one embodiment, the carboxyalkyl cellulose is carboxymethyl cellulose. The aqueous gel includes from about 60 to about 99% by weight carboxyalkyl cellulose based on the weight of the particle. In one embodiment, the aqueous gel includes from about 80 to about 95% by weight carboxyalkyl cellulose based on the weight of the particle. Suitable carboxyalkyl celluloses include carboxyalkyl celluloses (carboxymethyl cellulose) obtained from commercial sources.

The aqueous gel also includes a starch. The aqueous gel includes from about 1 to about 20% by weight starch based on the weight of the particles and, in one embodiment, the aqueous gel includes from about 1 to about 15% by weight starch based on the weight of the particles.

Starches are composed of two polysaccharides: amylose and amylopectin. Amylose is a linear polysaccharide having an average molecular weight of about 250,000 g/mole. Amylopectin is a branched polysaccharide (branching via 1,6-α-glucosidic links) having an average molecular weight of about 75,000,000 g/mole. Typically, the ratio of amylose to amylopectin is from about 1:4 to about 1:5.

Starches suitable for use in the present invention may be obtained from corn, wheat, maize, rice, sorghum, potato, cassava, barley, buckwheat, millet, oat, arrowroot, beans, peas, rye, tapioca, sago, and amaranth. Also suitable are waxy starches, such as from corn, wheat, maize, rice, sorghum, potato, cassava, and barley. Mixtures of starches can also be used.

Suitable starches for use in the invention include cooked and pre-gelatinized starches. Certain cooked and pre-gelatinized starches are commercially available from a variety of commercial sources.

In one embodiment, the starch is first cooked in water (e.g., 75° C. for 45 min). Then, an aqueous solution of a carboxyalkyl cellulose is added to the aqueous starch. A first crosslinking agent is added and mixed to obtain a crosslinked gel (e.g., intermolecular crosslinking of water-soluble polymers).

In the method, the aqueous gel including the carboxyalkyl cellulose and starch is treated with a first crosslinking agent to provide a crosslinked gel.

Suitable first crosslinking agents include crosslinking agents that are reactive towards hydroxyl groups and/or carboxyl groups. Representative crosslinking agents include metallic crosslinking agents, such as aluminum (III) compounds, titanium (IV) compounds, bismuth (III) compounds, boron (III) compounds, and zirconium (IV) compounds. The numerals in parentheses in the preceding list of metallic crosslinking agents refer to the valency of the metal.

Representative metallic crosslinking agents include aluminum sulfate; aluminum hydroxide; dihydroxy aluminum acetate (stabilized with boric acid); other aluminum salts of carboxylic acids and inorganic acids; other aluminum complexes, such as Ultrion 8186 from Nalco Company (aluminum chloride hydroxide); boric acid; sodium metaborate; ammonium zirconium carbonate (AZC); zirconium compounds containing inorganic ions or organic ions or neutral ligands; bismuth ammonium citrate (BAC); other bismuth salts of carboxylic acids and inorganic acids; titanium (IV) compounds, such as titanium (IV) bis(triethylaminato) bis (isopropoxide) (commercially available from the Dupont Company under the designation Tyzor TE); and other titanates with alkoxide or carboxylate ligands.

The first crosslinking agent is effective for intermolecularly crosslinking the carboxyalkyl cellulose (with or without carboxyalkyl hemicellulose) and starch molecules. The first crosslinking agent is applied in an amount of from about 0.1 to about 20% by weight based on the total weight of the particles.

The amount of crosslinking agent applied to the polymers will vary depending on the crosslinking agent. In general, the fibers having particles attached thereto have an aluminum content of about 0.01 to about 2.0% by weight based on the weight of the fibers for aluminum crosslinked particles, a titanium content of about 0.01 to about 4.5% by weight based on the weight of the fibers for titanium crosslinked particles, a zirconium content of about 0.01 to about 6.0% by weight based on the weight of the fibers for zirconium crosslinked particles; and a bismuth content of about 0.01 to about 5% by weight based on the weight of the fibers for bismuth crosslinked particles.

The crosslinked gel formed by treating the aqueous gel of a carboxyalkyl cellulose and a starch with a first crosslinking agent is then dried to provide a solid that is then comminuted to provide a plurality of particles (superabsorbent particles). In one embodiment, the particles are sieved to obtain particles having a size of from about 150 to about 1500 μm.

A portion of the plurality of particles (e.g., particles having a size of from about 150 to about 1500 μm) is combined with an aqueous dispersion of cellulose fibers that includes a first water-miscible solvent and, optionally, a second crosslinking agent, to provide a mixture that includes swollen particles and cellulose fibers. The ratio of superabsorbent particles to cellulose is from about 20:80 to about 80:20 by weight of the composition.

Suitable first water-miscible solvents include water-miscible alcohols and ketones. Representative first water-miscible solvents include acetone, methanol, ethanol, isopropanol, and mixtures thereof. In one embodiment, the first water-miscible solvent is ethanol. In another embodiment, the first water-miscible solvent is isopropanol.

Although available from other sources, suitable cellulosic fibers are derived primarily from wood pulp. Suitable wood pulp fibers for use with the invention can be obtained from well-known chemical processes such as the kraft and sulfite processes, with or without subsequent bleaching. Pulp fibers can also be processed by thermomechanical, chemithermomechanical methods, or combinations thereof. A high alpha cellulose pulp is also a suitable wood pulp fiber. The preferred pulp fiber is produced by chemical methods. Ground wood fibers, recycled or secondary wood pulp fibers, and bleached and unbleached wood pulp fibers can be used. Softwoods and hardwoods can be used. Suitable fibers are commercially available from a number of companies, including Weyerhaeuser Company. For example, suitable cellulosic fibers produced from southern pine that are usable with the present invention are available from Weyerhaeuser Company under the designations CF416, NF405, PL416, FR516, and NB416. Other suitable fibers include northern softwood and eucalyptus fibers.

The use of a crosslinking agent will depend on the nature of the superabsorbent particles to be adhered to the fibers. If the superabsorbent particles are highly crosslinked, added crosslinking agent is not required. However if the superabsorbent particles are not highly crosslinked, then the second crosslinking agent is used.

Suitable second crosslinking agents include crosslinking agents that are reactive toward hydroxyl groups and/or carboxyl groups. The second crosslinking agent can be the same as or different from the first crosslinking agent. Representative second crosslinking agents include the metallic crosslinking agents noted above useful as the first crosslinking agents. The second crosslinking agent may be the same as or different from the first crosslinking agent. Mixtures of two or more crosslinking agents in different ratios may be used in each crosslinking step.

The second crosslinking agent is applied in an amount up to about 20 percent by weight based on the total weight of fibers having particles attached thereto.

To the aqueous dispersion containing the swollen particles, cellulose fibers, first water-miscible solvent, and optional second crosslinking agent (mixture) is then added a second water-miscible solvent to provide the fibers having particles attached thereto. Suitable second water-miscible solvents also include water-miscible alcohols and ketones. Representative second water-miscible solvents include acetone, methanol, ethanol, isopropanol, and mixtures thereof. In one embodiment, the second water-miscible solvent is ethanol. In another embodiment, the second water-miscible solvent is isopropanol. In one embodiment, the first and second water-miscible solvents are the same.

In one embodiment, the second crosslinking agent is added after adding the second water-miscible solvent.

The ratio of first water-miscible solvent to water can be from about 5:95 by volume to about 50:50 by volume. In one embodiment, the ratio of first water-miscible solvent to water is about 40:60 by volume.

The ratio of combined (first and second) water-miscible solvents to water is at least 60% by volume. In one embodiment, the ratio is at least 70% by volume.

In the method, mixing the mixture of swollen particles and cellulose fibers with the second water-miscible solvent includes stirring to provide the fibers having particles attached thereto. The mixing step and the use of the second water-miscible solvent control the rate of dehydration and solvent exchange and provides for the fibers having particles attached thereto. Mixing can be carried out using a variety of devices including overhead stirrers, Hobart mixers, British disintegrators, and blenders. For these mixing devices, the blender provides the greatest shear and the overhead stirrer provides the least shear.

The product fibers having particles attached thereto can be obtained by filtration. In one embodiment, the wet fibers having particles attached thereto is partially dried in an oven below 80° C. In one embodiment, the partially-dried fibers having particles attached thereto is then fiberized and dried in an oven below 80° C.

The fibers having particles attached thereto prepared as described above includes a plurality of cellulose fibers to which are adhered superabsorbent particles derived from a combination of a carboxyalkyl cellulose and a starch.

The fibers having particles attached thereto are prepared by a process that includes optionally treating an aqueous suspension of a plurality of particles (prepared by crosslinking a carboxyalkyl cellulose and a starch with a first crosslinking agent) and an aqueous dispersion of cellulose fibers and a first water-miscible solvent with a second crosslinking agent to provide a mixture that includes swollen particles and cellulose fibers, and then adding a second water-miscible solvent to the mixture.

The fibers having particles attached thereto are insoluble in water while being capable of absorbing water. The fibers having particles attached thereto are rendered water insoluble, in part, by a plurality of non-permanent interpolymer metal crosslinks.

The fibers having particles attached thereto includes particles having intermolecular metal crosslinks between polymer molecules. The metal crosslink arises as a consequence of an associative interaction (e.g., bonding) between functional groups of the particle polymers (e.g., carboxy, carboxylate, or hydroxyl groups) and a multi-valent metal species (see description of crosslinking agents above). Suitable multi-valent metal species include metal ions having a valency of three or greater and that are capable of forming an associative interaction with a polymer (e.g., reactive toward associative interaction with the polymer's carboxy, carboxylate, or hydroxyl groups). The polymers are intermolecularly crosslinked when the multi-valent metal species forms an associative interaction with functional groups on two or more polymer molecules. A crosslink may be formed within one polymer molecule or may be formed between two or more polymer molecules. The extent of crosslinking affects the water solubility of the particles and the ability of the particles to swell on contact with an aqueous liquid.

The superabsorbent particles include non-permanent metal crosslinks formed both intermolecularly and intramolecularly in the population of polymer molecules. As used herein, the term "non-permanent crosslink" refers to the metal crosslink formed with two or more functional groups of a polymer molecule (intramolecularly) or formed with two or more functional groups of two or more polymer molecules (intermolecularly). It will be appreciated that the process of dissociating and re-associating (breaking and reforming crosslinks) the multi-valent metal ion and polymer molecules is dynamic and also occurs during liquid acquisition. During water acquisition the individual particles attached to treated cellulose swell and change to gel state. The ability of non-permanent metal crosslinks to dissociate and associate under water acquisition imparts greater freedom to the gels to expand than if it was restrictively crosslinked by permanent crosslinks that do not have the ability to dissociate and reassociate. Covalent organic crosslinks such as ether crosslinks are permanent crosslinks that do not have the ability to dissociate and reassociate.

Figure 2:
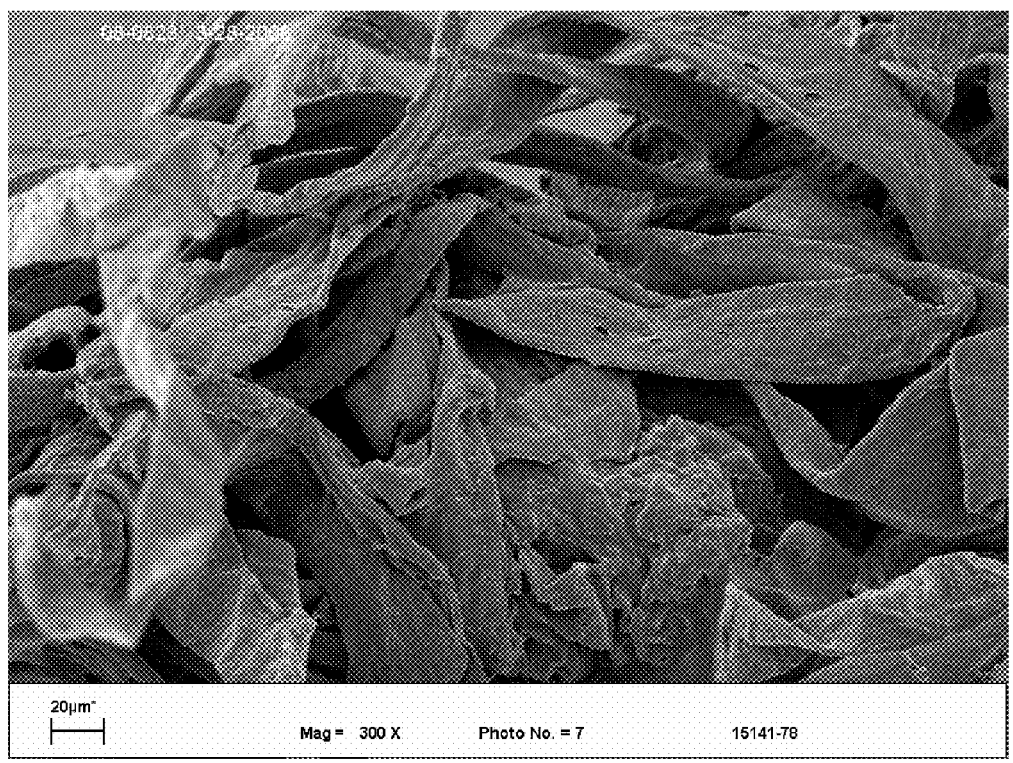
FIG. 2 is a scanning electron microscope photograph (300×) of representative fibers having particles attached thereto (Sample 4, Table 2) formed in accordance with the present invention.
Figure 3:
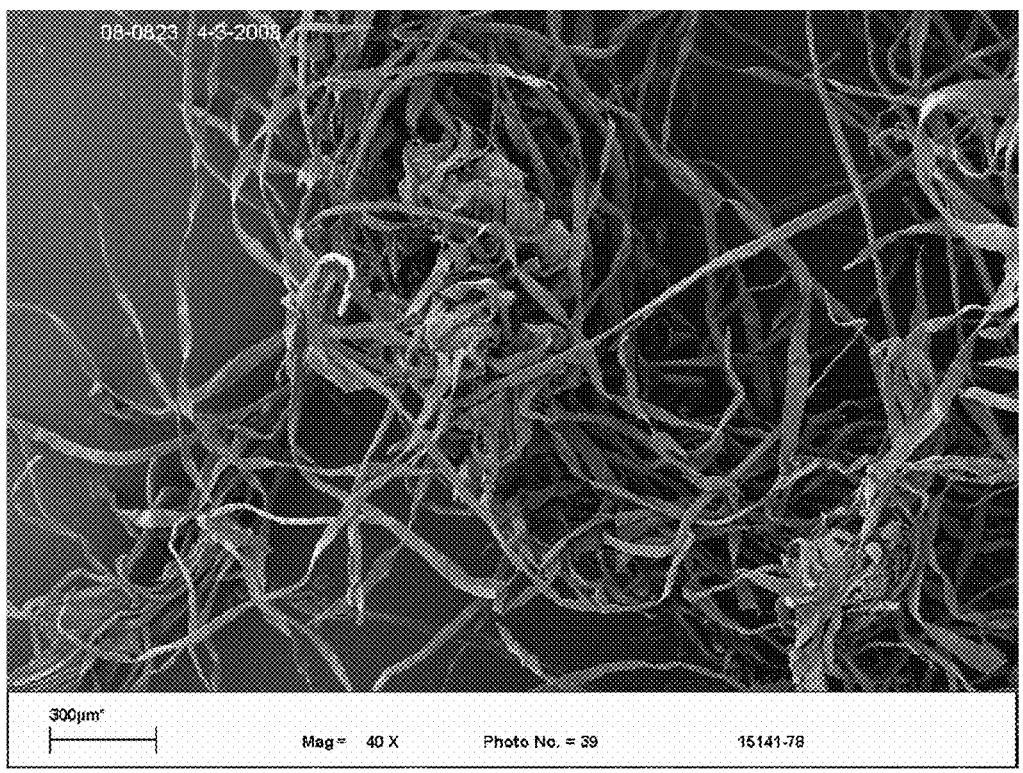
FIG. 3 is a scanning electron microscope photograph (40×) of representative fibers having particles attached thereto (Sample 4, Table 2) formed in accordance with the present invention.

Representative fibers having particles attached thereto formed in accordance with the invention are shown in FIGS. 1-3. FIG. 1 is a scanning electron microscope photograph (50×) of representative fibers having particles attached thereto (Sample 4, Table 2). FIG. 2 is a scanning electron microscope photograph (300×) of representative fibers having particles attached thereto (Sample 4, Table 2). FIG. 3 is a scanning electron microscope photograph (40×) of representative fibers having particles attached thereto (Sample 4, Table 2).

The composition of fibers having particles attached thereto are highly absorptive. The composition has a Free Swell Capacity of from about 30 to about 60 g/g (0.9% saline solution) and a Centrifuge Retention Capacity (CRC) of from about 15 to about 40 g/g (0.9% saline solution).

The composition of fibers having particles attached thereto are water insoluble and water swellable. Water insolubility of the particles is imparted by intermolecular crosslinking of the polymer molecules, and water swellability is imparted to the absorbent particles by the presence of carboxylate anions with associated cations. The composition is characterized as having a relatively high liquid absorbent capacity for water (e.g., pure water or aqueous solutions, such as salt solutions or biological solutions such as urine). Furthermore, because of the fibrous nature of the composition, the composition also possesses the ability to wick liquids.

The fibers having particles attached thereto are useful as a superabsorbent composition in personal care absorbent products (e.g., infant diapers, feminine care products, and adult incontinence products). Because of their ability to wick liquids and to absorb liquids, the composite is useful in a variety of other applications, including, for example, wound dressings, cable wrap, absorbent sheets or bags, and packaging materials.

The preparations of representative superabsorbent particles useful in adhering to cellulose fibers are described in Examples 1-5. In these examples gels of a representative carboxyalkyl cellulose and a starch are crosslinked with a metallic crosslinking agent. The crosslinked gel is then dried and ground to provide particles (flakes). The composition and liquid absorbent characteristics of representative superabsorbent particles (flakes) useful in making the fibers are summarized in Table 1. The preparations of representative superabsorbent fibers having particles attached thereto are described in Examples 1-5. The composition and liquid absorbent characteristics of representative superabsorbent fibers having particles attached thereto are summarized in Table 2. In the Table 1, "DS" refers to the carboxymethyl cellulose (CMC) degree of substitution, viscosity (cps) refers to Brookfield viscosity determined with spindle #3 at 20 rpm at 25° C., and "$Al_2(SO_4)_3$" refers to aluminum sulfate octadecahydrate. The percentages of the CMC and starch refer to the percent by weight of each component based on the total weight of the product. In Table 1, the percentage for the crosslinking agent is the amount of crosslinking agent applied to the CMC and starch.

Test Methods

Free Swell and Centrifuge Retention Capacities

The materials, procedure, and calculations to determine free swell capacity (g/g) and centrifuge retention capacity (CRC) (g/g) were as follows.

Test Materials:

Japanese pre-made empty tea bags (available from Drugstore.com, IN PURSUIT OF TEA polyester tea bags 93 mm×70 mm with fold-over flap (http:www.mesh.ne.jp/tokiwa/)).

Balance (4 decimal place accuracy, 0.0001 g for air-dried superabsorbent polymer (ADS SAP) and tea bag weights); timer; 1% saline; drip rack with clips (NLM 211); and lab centrifuge (NLM 211, Spin-X spin extractor, model 776S, 3,300 RPM, 120v).

Test Procedure

1. Determine solids content of ADS
2. Pre-weigh tea bags to nearest 0.001 g and record.
3. Accurately weigh 0.2025 g+/−0.0025 g of test material (SAP), record and place into pre-weighed tea bag (air-dried (AD) bag weight). (ADS weight+AD bag weight=total dry weight).
4. Fold tea bag edge over closing bag.
5. Fill a container (at least 3 inches deep) with at least 2 inches with 1% saline.
6. Hold tea bag (with test sample) flat and shake to distribute test material evenly through bag.
7. Lay tea bag onto surface of saline and start timer.
8. Soak bags for specified time (e.g., 30 minutes).
9. Remove tea bags carefully, being careful not to spill any contents from bags, hang from a clip on drip rack for 3 minutes.
10. Carefully remove each bag, weigh, and record (drip weight).
11. Place tea bags onto centrifuge walls, being careful not to let them touch and careful to balance evenly around wall.
12. Lock down lid and start timer. Spin for 75 seconds.
13. Unlock lid and remove bags. Weigh each bag and record weight (centrifuge weight).

Calculations:

The tea bag material has an absorbency determined as follows:

Free Swell Capacity, factor=5.78
Centrifuge Capacity, factor=0.50
Z=Oven dry SAP wt (g)/Air dry SAP wt (g)
Free Capacity (g/g):

$$\frac{[(\text{drip wt}(g) - \text{dry bag wt}(g)) - (AD\ SAP\ \text{wt}(g))] - (\text{dry bag wt}(g) * 5.78)}{(AD\ SAP\ \text{wt}(g) * Z)}$$

Centrifuge Retention Capacity (g/g):

$$\frac{[\text{centrifuge wt}(g) - \text{dry bag wt}(g) - (AD\ SAP\ \text{wt}(g))] - (\text{dry bag wt}(g) * 0.50)}{(AD\ SAP\ \text{wt} * Z)}$$

The following examples are provided for the purpose of illustrating, not limiting, the invention.

EXAMPLES

Example 1

The Preparation of Representative Superabsorbent Fibers having Particles Attached thereto: Aluminum Sulfate Crosslinking In this example, the preparation of representative superabsorbent fibers having particles attached thereto is described. See Sample 1, Tables 1 and 2.

Superabsorbent particles. Corn starch (Clinton 185®, Archer Daniel Midland, Ill.) (2.4 g) was cooked for 45 minutes at 75° C. in 51 mL deionized water. The cooked starch was then added to 899 mL deionized water in a Hobart mixer. Then, carboxymethyl cellulose (40 g OD northern pine wood pulp CMC, DS 1.07, 1% aqueous solution, Brookfield viscosity 725 cps, spindle #3 and speed 20 rpm) was added with mixing. The aqueous polymer mixture was mixed for 60 minutes.

To the aqueous polymer mixture was added 0.6 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to two TEFLON coated baking pans (10 inch×17 inch) and dried at 65° C. in a safety oven to provide a film. The dried film was ground into particles for testing. Particles having sizes from 74 to 300 μm and from 300 to 850 μm were tested. The particles had free swell (51.6 g/g) and centrifuge retention capacity (30.7 g/g) for 0.9% saline solution.

Superabsorbent fibers having particles attached thereto. Fluff pulp (NB 416, Weyerhaeuser Company) (10 g) was dispersed in 750 mL deionized water with efficient mixing for 5 minutes. Isopropanol (500 mL) was then added and mixed well for 5 minutes using an overhead mixer. Superabsorbent particles (15.0 g, 300-850 µm), prepared as described above, were added to the water/isopropanol mixture and the swelling mass was mixed for 5 minutes. Isopropanol (835 mL) was added to the mixture and further mixed for 15 minutes. The fiber mass was collected by filtration and dried in an oven at 65° C. for 15 minutes. Before the fiber mass was completely dried, the mass was placed in a blender and fiberized. The product was finally dried in an oven at 65° C. The superabsorbent fibers having particles attached thereto had free swell (41.4 g/g) and centrifuge retention capacity (21.0 g/g) for 0.9% saline solution.

Example 2

The Preparation of Representative Superabsorbent Fibers having Particles Attached thereto; Aluminum, Sulfate Crosslinking In this example, the preparation of representative superabsorbent fibers having particles attached thereto is described. See Sample 2, Tables 1 and 2.

Superabsorbent particles. Corn starch (Clinton 185®, Archer Daniel Midland, Ill.) (2.4 g) was cooked for 45 minutes at 75° C. in 54 mL deionized water. The cooked starch was then added to 896 mL deionized water in a Hobart mixer. Then, carboxymethyl cellulose (40 g OD northern pine wood pulp CMC, DS 1.03, 1% aqueous solution, Brookfield viscosity 1465 cps, spindle #3 and speed 20 rpm) was added with mixing. The aqueous polymer mixture was mixed for 60 minutes.

To the aqueous polymer mixture was added 1.0 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to four TEFLON coated baking pans (10 inch×17 inch) and dried at 65° C. in a safety oven to provide a film. The dried film was ground into particles for testing. Particles having sizes from 74 to 300 µm and from 300 to 850 µm were tested. The particles had free swell (41.6 g/g) and centrifuge retention capacity (28.2 g/g) for 0.9% saline solution.

Superabsorbent fibers having particles attached thereto. Fluff pulp (NB 416, Weyerhaeuser Company) (10 g) was dispersed in 750 mL deionized water with efficient mixing for 5 minutes. Isopropanol (50 mL) was then added and mixed well for 5 minutes using an overhead mixer. Superabsorbent particles (15.0 g, 300-850 µm), prepared as described above, were added to the water/isopropanol mixture and the swelling mass was mixed for 5 minutes. Isopropanol (835 mL) was added to the mixture and further mixed for 15 minutes. The fiber mass was collected by filtration and dried in an oven at 65° C. for 15 minutes. Before the fiber mass was completely dried, the mass was placed in a blender and fiberized. The product was finally dried in an oven at 65° C.

The superabsorbent fibers having particles attached thereto had free swell (37.9 g/g) and centrifuge retention capacity (16.4 g/g) for 0.9% saline solution.

Example 3

The Preparation of Representative Superabsorbent Fibers having Particles Attached thereto: Aluminum Sulfate Crosslinking In this example, the preparation of representative superabsorbent fibers having particles attached thereto is described. See Sample 3, Tables 1 and 2.

Superabsorbent particles. Corn starch (Clinton 185®, Archer Daniel Midland, Ill.) (2.4 g) was cooked for 45 minutes at 75° C. in 47 mL deionized water. The cooked starch was then added to 903 mL deionized water in a Hobart mixer. Then, carboxymethyl cellulose (40 g OD northern pine wood pulp CMC, DS 1.03, 1% aqueous solution, Brookfield viscosity 1465 cps, spindle #3 and speed 20 rpm) was added with mixing. The aqueous polymer mixture was mixed for 60 minutes.

To the aqueous polymer mixture was added 0.8 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to four TEFLON coated baking pans (10 inch×17 inch) and dried at 65° C. in a safety oven to provide a film. The dried film was ground into particles for testing. Particles having sizes from 74 to 300 µm and from 300 to 850 µm were tested. The particles had free swell (43.1 g/g) and centrifuge retention capacity (28.4 g/g) for 0.9% saline solution.

Superabsorbent fibers having particles attached thereto. Fluff pulp (NB 416, Weyerhaeuser Company) (10 g) was dispersed in 750 mL deionized water with efficient mixing for 5 minutes. Isopropanol (500 mL) was then added and mixed well for 5 minutes using an overhead mixer. Superabsorbent particles (15.0 g, 300-850 µm), prepared as described above, were added to the water/isopropanol mixture and the swelling mass was mixed for 5 minutes. Isopropanol (835 mL) was added to the mixture and further mixed for 15 minutes. The fiber mass was collected by filtration and dried in an oven at 65° C. for 15 minutes. Before the fiber mass was completely dried, the mass was placed in a blender and fiberized. The product was finally dried in an oven at 65° C. The superabsorbent fibers having particles attached thereto had free swell (40.6 g/g) and centrifuge retention capacity (18.9 g/g) for 0.9% saline solution.

Example 4

The Preparation of Representative Superabsorbent Fibers having Particles Attached thereto: Aluminum Sulfate Crosslinking In this example, the preparation of representative superabsorbent fibers having particles attached thereto is described. See Sample 4, Tables 1 and 2.

Superabsorbent particles. Corn starch (Clinton 185®, Archer Daniel Midland, Ill.) (2.4 g) was cooked for 45 minutes at 75° C. in 48 mL deionized water. The cooked starch was then added to 902 mL deionized water in a Hobart mixer. Then, carboxymethyl cellulose (40 g OD northern pine wood pulp CMC, DS 0.93, 1% aqueous solution, Brookfield viscosity 1350 cps, spindle #3 and speed 20 rpm) was added with mixing. The aqueous polymer mixture was mixed for 60 minutes.

To the aqueous polymer mixture was added 0.2 g aluminum sulfate octadecahydrate (Sigma Aldrich, Wis.) in 50 mL deionized water. The polymer mixture was then mixed for 30 minutes to provide a crosslinked polymer gel.

The crosslinked polymer gel was then applied as a coating to four TEFLON coated baking pans (10 inch×17 inch) and dried at 65° C. in a safety oven to provide a film. The dried film was ground into particles for testing. Particles having sizes from 74 to 300 μm and from 300 to 850 μm were tested. The particles had free swell (61.6 g/g) and centrifuge retention capacity (46.2 g/g) for 0.9% saline solution.

Superabsorbent fibers having particles attached thereto. Fluff pulp (NB 416, Weyerhaeuser Company) (10 g) was dispersed in 750 mL deionized water with efficient mixing for 5 minutes. Isopropanol (500 mL) was then added and mixed well for 5 minutes using an overhead mixer. Superabsorbent particles (15.0 g, 300-850 μm), prepared as described above, were added to the water/isopropanol mixture and the swelling mass was mixed for 5 minutes. Isopropanol (835 mL) was added to the mixture and further mixed for 15 minutes. The fiber mass was collected by filtration and dried in an oven at 65° C. for 15 minutes. Before the fiber mass was completely dried, the mass was placed in a blender and fiberized. The product was finally dried in an oven at 65° C. The superabsorbent fibers having particles attached thereto had free swell (46.1 g/g) and centrifuge retention capacity (29.5 g/g) for 0.9% saline solution.

Example 5

The Preparation of Representative Superabsorbent Fibers having Particles Attached thereto: Aluminum Sulfate Crosslinking In this example, the preparation of representative superabsorbent fibers having particles attached thereto is described. See Sample 5, Tables 1 and 2.

Superabsorbent particles. Corn starch (Clinton 185®, Archer Daniel Midland, IL.) (60 g) was cooked for 45 minutes at 75° C. in 1.0 L deionized water. The cooked starch was then added to 22.75 L deionized water in a Hobart mixer. Then, carboxymethyl cellulose (1000 g OD northern pine wood pulp CMC, DS 0.93, 1% aqueous solution, Brookfield viscosity 1350 cps, spindle #3 and speed 20 rpm) was added with mixing. The aqueous polymer mixture was mixed for 60 minutes.

To the aqueous polymer mixture was added 5.0 g aluminum sulfate octadecahydrate (Sigma Aldrich, Wis.) in 1.25 L deionized water. The polymer mixture was then mixed for 30 minutes to provide a crosslinked polymer gel.

The crosslinked polymer gel was then applied as a coating to two TEFLON coated baking pans (10 inch×17 inch) and dried at 65° C. in a safety oven to provide a film. The dried film was ground into particles for testing. Particles having sizes from 74 to 300 μm and from 300 to 850 μm were tested. The particles had free swell (54.2 g/g) and centrifuge retention capacity (39.4 g/g) for 0.9% saline solution.

Superabsorbent fibers having particles attached thereto. Fluff pulp (NB 416, Weyerhaeuser Company) (20 g) was dispersed in 1500 mL deionized water with efficient mixing for 5 minutes. Superabsorbent particles (30.0 g, 300-850 μm), prepared as described above, were added to the mixture and the swelling mass was mixed for 5 minutes. Isopropanol (1000 mL) was added to the mixture and mixed welt for 5 minutes using an overhead mixer. Isopropanol (1670 mL) was added to the mixture and further mixed for 15 minutes. The fiber mass was collected by filtration and dried in an oven at 65° C. for 15 minutes. Before the fiber mass was completely dried, the mass was placed in a blender and fiberized. The product was finally dried in an oven at 65° C. The superabsorbent fibers having particles attached thereto had free swell (42.4 g/g) and centrifuge retention capacity (25.1 g/g) for 0.9% saline solution.

TABLE 1

Superabsorbent Flakes From Crosslinked Aqueous Mixtures of CMC and Starch

| Sample | CMC (DS, viscosity, %) | Starch (wgt % total wgt) | Crosslinking agent (wgt % total wgt, applied) | Free Swell (g/g) | CRC (g/g) |
|---|---|---|---|---|---|
| 1 | 1.07, 725, 93.7 | 5.6 | $Al_2(SO_4)_3$, 0.7 | 51.6 | 30.7 |
| 2 | 1.03, 1465, 93.2 | 5.6 | $Al_2(SO_4)_3$, 1.2 | 41.6 | 28.2 |
| 3 | 1.03, 1465, 93.5 | 5.6 | $Al_2(SO_4)_3$, 0.9 | 43.1 | 28.4 |
| 4 | 0.93, 1370, 94.1 | 5.7 | $Al_2(SO_4)_3$, 0.2 | 61.6 | 46.2 |
| 5 | 0.93, 1370, 94.1 | 5.7 | $Al_2(SO_4)_3$, 0.2 | 54.1 | 39.4 |

TABLE 2

Superabsorbent Fiber From CMC/Starch Flakes and Cellulose Fiber

| Sample | CMC/Starch flake (wgt % total wgt) | Cellulose Fiber (wgt % total wgt) | Free Swell (g/g) | CRC (g/g) |
|---|---|---|---|---|
| 1 | 60 | 40 | 41.4 | 21.0 |
| 2 | 60 | 40 | 37.9 | 16.4 |
| 3 | 60 | 40 | 40.6 | 18.9 |
| 4 | 60 | 40 | 46.1 | 29.5 |
| 5 | 60 | 40 | 42.4 | 25.1 |

While illustrative embodiments have been illustrated and described, it will be appreciated that various changes can be made therein without departing from the spirit and scope of the invention.

The invention claimed is:

1. A method for making fibers having particles attached thereto, comprising:
    (a) blending a carboxyalkyl cellulose and a starch in water to provide an aqueous gel;
    (b) treating the aqueous gel with a first crosslinking agent to provide a crosslinked gel;
    (c) drying the crosslinked gel to provide a solid;
    (d) comminuting the solid to provide a plurality of particles;
    (e) combining at least a portion of the plurality of particles with a aqueous dispersion comprising cellulose fibers and a first water-miscible solvent and, optionally, a second crosslinking agent, to provide a mixture comprising swollen particles and cellulose fibers; and
    (f) adding a second water-miscible solvent to the mixture to provide fibers having particles attached thereto.

2. The method of claim 1 further comprising adding the second crosslinking agent only after adding the second water-miscible solvent.

3. The method of claim 1, further comprising drying the fibers having particles attached thereto to provide partially-dried fibers having particles attached thereto.

4. The method of claim 3, further comprising fiberizing the partially-dried fibers to provide partially-dried fiberized fibers having particles attached thereto.

5. The method of claim 4, further comprising drying the partially-dried fiberized fibers to provide dried, fiberized fibers having particles attached thereto.

6. The method of claim 1, wherein the carboxyalkyl cellulose has a degree of carboxyl group substitution of from about 0.3 to about 2.5.

7. The method of claim 1, wherein the carboxyalkyl cellulose is carboxymethyl cellulose.

8. The method of claim 1, wherein the starch is selected from the group consisting of corn, wheat, maize, rice, sorghum, potato, cassava, barley, buckwheat, millet, oat, arrowroot, beans, peas, rye, tapioca, sago, and amaranth starches.

9. The method of claim 1, wherein the aqueous gel comprises from about 60 to about 99 percent by weight carboxyalkyl cellulose based on the total weight of particles.

10. The method of claim 1, wherein the aqueous gel comprises from about 1 to about 20 percent by weight starch based on the total weight of particles.

11. The method of claim 1, wherein the first crosslinking agent is selected from the group consisting of aluminum (III) compounds, titanium (IV) compounds, bismuth (III) compounds, boron (III) compounds, and zirconium (IV) compounds.

12. The method of claim 1, wherein the first crosslinking agent is present in an amount from about 0.1 to about 20 percent by weight based on the total weight of particles.

13. The method of claim 1, wherein the second crosslinking agent is selected from the group consisting of aluminum (III) compounds, titanium (IV) compounds, bismuth (III) compounds, boron (III) compounds, and zirconium (IV) compounds.

14. The method of claim 1, wherein the second crosslinking agent is present in an amount up to about 20 percent by weight based on the total weight of composite fibers.

15. The method of claim 1, wherein the first water-miscible solvent is an alcohol.

16. The method of claim 1, wherein the first water-miscible solvent is selected from the group consisting of methanol, ethanol, isopropanol, and mixtures thereof.

17. The method of claim 1, wherein the second water-miscible solvent is an alcohol.

18. The method of claim 1, wherein the second water-miscible solvent is selected from the group consisting of methanol, ethanol, isopropanol, and mixtures thereof.

* * * * *